(12) United States Patent
Hirschbein et al.

(10) Patent No.: US 8,445,412 B2
(45) Date of Patent: May 21, 2013

(54) SEPARATION OF PYROPHOSPHATE RELEASE AND PYROPHOSPHATE DETECTION

(75) Inventors: Bernard Hirschbein, Hayward, CA (US); Filiz Gorpe-Yasar, Hayward, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/203,463

(22) PCT Filed: Feb. 24, 2010

(86) PCT No.: PCT/US2010/025273
§ 371 (c)(1),
(2), (4) Date: Aug. 25, 2011

(87) PCT Pub. No.: WO2010/099230
PCT Pub. Date: Sep. 2, 2010

(65) Prior Publication Data
US 2011/0306521 A1 Dec. 15, 2011

Related U.S. Application Data

(60) Provisional application No. 61/155,424, filed on Feb. 25, 2009.

(51) Int. Cl.
| | | |
|---|---|---|
| *C12Q 1/66* | (2006.01) | |
| *C12Q 1/68* | (2006.01) | |
| *C12Q 1/48* | (2006.01) | |
| *C12Q 1/42* | (2006.01) | |
| *C40B 40/06* | (2006.01) | |
| *C40B 50/14* | (2006.01) | |

(52) U.S. Cl.
USPC .............. 506/16; 435/6.1; 435/15; 435/8; 435/4; 435/21; 435/18; 506/30

(58) Field of Classification Search
USPC ............................... 506/16; 435/6.1
See application file for complete search history.

(56) References Cited

U.S. PATENT DOCUMENTS

| 4,724,042 | A | * | 2/1988 | Sherman ................ 216/90 |
|---|---|---|---|---|
| 5,744,320 | A | | 4/1998 | Sherf et al. |
| 6,210,891 | B1 | * | 4/2001 | Nyren et al. ............. 435/6.12 |
| 6,258,568 | B1 | | 7/2001 | Nyren |

(Continued)

FOREIGN PATENT DOCUMENTS

| KR | 10-2003-0069803 | 8/2003 |
|---|---|---|
| KR | 10-0810007 | 3/2008 |

(Continued)

OTHER PUBLICATIONS

Agah, et al., "A High-Resolution Low-Power Oversampling ADC with Extended-Range for Bio-Sensor Arrays" *IEEE Symposium* (2007) 244-245.

(Continued)

*Primary Examiner* — Ardin Marschel
*Assistant Examiner* — Richard L Manteuffel
(74) *Attorney, Agent, or Firm* — John T. Murphy

(57) ABSTRACT

The present technology relates to methods and systems for detection of pyrophosphate. As such, disclosed herein are methods and systems that permit improved pyrophosphate detection. Also disclosed herein are methods and systems which utilize improved pyrophosphate detection for nucleotide sequencing.

48 Claims, 1 Drawing Sheet

U.S. PATENT DOCUMENTS

| | | |
|---|---|---|
| 6,274,320 B1 | 8/2001 | Rothberg et al. |
| 6,355,431 B1 | 3/2002 | Chee et al. |
| 2002/0102578 A1 | 8/2002 | Dickinson et al. |
| 2005/0119497 A1 | 6/2005 | Hong et al. |
| 2008/0293128 A1 | 11/2008 | Yukimasa et al. |

FOREIGN PATENT DOCUMENTS

| | | |
|---|---|---|
| WO | 98/13523 | 4/1998 |
| WO | WO 98/13523 | 4/1998 |
| WO | WO 98/28440 | 7/1998 |
| WO | WO 00/63437 | 10/2000 |
| WO | WO 2008/079905 | 7/2008 |
| WO | 2008/130092 | 10/2008 |

OTHER PUBLICATIONS

Balharry and Nicholas, "New Assay for ATP-Sulphurylase Using the Lucifering-Luciferase Method" *Anal. Biochem.* (1971) 40: 1-17.

Blum, et al., "Design of Luminescence Photobiosensors" *J. Biolumin. Chemilumin.* (1989) 4: 543-550.

Bronks, et al., "Combined Imaging and Chemical Sensing Using a Single Optical Imaging Fiber" *Anal. Chem.* (1995) 67: 2750-2757.

Cook, et al., "A Rapid, Enzymatic Assay for the Measurement of Inorganic Pyrophosphate in Animal Tissues" *Anal. Biochem.* (1978) 91: 557-565.

Daley, et al., "ATP Sulfurylase-Dependent Assays for Inorganic Pyrophosphate: Applications to Determining the Equilibrium Constant and Reverse Direction Kinetics of the Pyrophosphatase Reaction, Magnesium Binding to Orthophosphate, and Unknown Concentrations of Pyrophosphate" *Anal. Biochem.* (1986) 157: 385-395.

Drake, et al., "A New, Convenient Method for the Rapid Analysis of Inorganic Pyrophosphate" *Anal. Biochem.* (1979) 94: 117-120.

Eltoukhy, et al., "A 0.18um CMOS bioluminescence detection lab-on-chip" *IEEE J. of Solid-State Circuits* (2006) 41(3): 651-662.

Green and Kricka, "Rapid assays based on immobilized bioluminescent enzymes and photographic detection of light emission" *Talanta* (1984) 31(3): 173-176.

Guillory, et al., "Measurement of Simultaneous Synthesis of Inorganic Pyrophosphate and Adenosine Triphosphate" *Anal. Biochem.* (1971) 39: 170-180.

Hampf, Mathias and Manfred Gossen, "A protocol for combined *Photinus* and *Renilla* luciferase quantification compatible with protein assays" *Anal. Biochem.* (2006) 356: 94-99.

Hawes and Nicholas, "Adenosine 5'-Triphosphate Sulphurylase from *Saccharomyces cerevisiae*" *Biochem. J.* (1973) 133: 541-550.

Heller, et al., "'Wired' Enzyme Electrodes for Amperometric Determination of Glucose or Lactate in the Presence of Interfering Substances" *Anal. Chem.* (1994) 66: 2451-2457.

Johnson, et al., "An Enzymic Method for Determination of Inorganic Pyrophosphate and Its Use as an Assay for RNA Polymerase" *Anal. Biochem.* (1968) 26: 137-145.

Kricka, "Chemiluminescent and bioluminescent techniques" *Clin. Chem.* (1991) 37: 1472-1481.

Leach, Franklin R., "ATP Determination with Firefly Luciferase" *J. Appl. Biochem.* (1981) 3: 473-517.

Lovgren, et al., "Continuous monitoring of NADH-converting reactions by bacterial luminescence" *J. Appl. Biochem.* (1982) 4: 103-111.

Lundin, Arne, "Applications of firefly luciferase", In: *Luminescent Assays* (1982) Raven Press, New York.

Nyren, Pal, "Enzymatic Method for Continuous Monitoring of DNA Polymerase Activity" *Anal. Biochem.* (1987) 167: 235-238.

Nyren, et al., "Solid Phase DNA Minisequencing by an Enzymatic Luminometric Inorganic Pyrophosphate Detection Assay" *Anal. Biochem.* (1993) 208: 171-175.

Ohara, et al., Glucose Electrodes Based on Cross-Linked $[Os(bpy)_2Cl]^{+/2+}$ Complexed Poly(1-vinylimidazole) Films *Anal. Chem.* (1993) 65: 3512-3517.

Reeves, Richard E. and Lamar K. Malin, "Enzymic Assay Method for Inorganic Pyrophosphate" *Anal. Biochem.* (1969) 28: 282-287.

Renosto, et al., "Regulation of Inorganic Sulfate Activation in Filamentous Fungi" *J. Biol. Chem.* (1990) 265: 10300-10308.

Robbins and Lipmann, "Enzymatic Synthesis of Adenosine-5'-Phosphosulfate" *J. Biol. Chem.* (1958) 233: 686-690.

Ronaghi, et al., "Analyses of Secondary Structures in DNA by Pyrosequencing" *Anal. Biochem.* (1999) 267: 65-71.

Ronaghi, et al., "Real-Time DNA Sequencing Using Detection of Pyrophosphate Release" *Anal. Biochem.* (1996) 242: 84-89.

Ronaghi, et al., "A Sequencing Method Based on Real-Time Pyrophosphate" *Science* (1998) 281: 363-365.

Schultz, et al., "Bioluminometric Assay of ADP and ATP at High ATP/ADP Ratios: Assay of ADP after Enzymatic Removal of ATP" *Anal. Biochem.* (1993) 215: 302-304.

Segel, et al., "Sulfate-Activating Enzymes" *Methods Enzymol.* (1987) 143: 334-349.

Selinger, H. H., and W. D. McElroy, "Spectral Emission and Quantum Yield of Firefly Bioluminescence" *Arch. Biochem. Biophys.* (1960) 88: 136-145.

Seubert, et al., "ATP Sulfurylase from *Penicillium chrysogenum*: Measurements of the True Specific Activity of an Enzyme Subject to Potent Product Inhibition and a Reassessment of the Kinetic Mechanism" *Arch. Biochem. Biophys.* (1983) 225: 679-691.

Seubert, et al., "Adenosinetriphosphate Sulfurylase from *Penicillium chryosgenum*: Steady-State Kinetics of the Forwardand Reverse Rections, Alternative Substrate Kinetics, and Equilibrium Binding Studies" *Arch. Biochem. Biophys.* (1985) 240(2): 509-523.

Wilson and Bandurski, "Enzymatic Reactions Involving Sulfate, Sulfite, Selenate, and Molybdate" *J. Biol. Chem.* (1958) 233: 975-981.

International Search Report, dated Oct. 11, 2010, issued in International Application No. PCT/US2010/025273.

Lee, Dong Hoon et al., "An azophenol-based chromogenic pyrophosphate sensor in water", Journal of the American Chemical Society, vol. 125, No. 26, Jul. 2, 2003, 7752-7753.

* cited by examiner

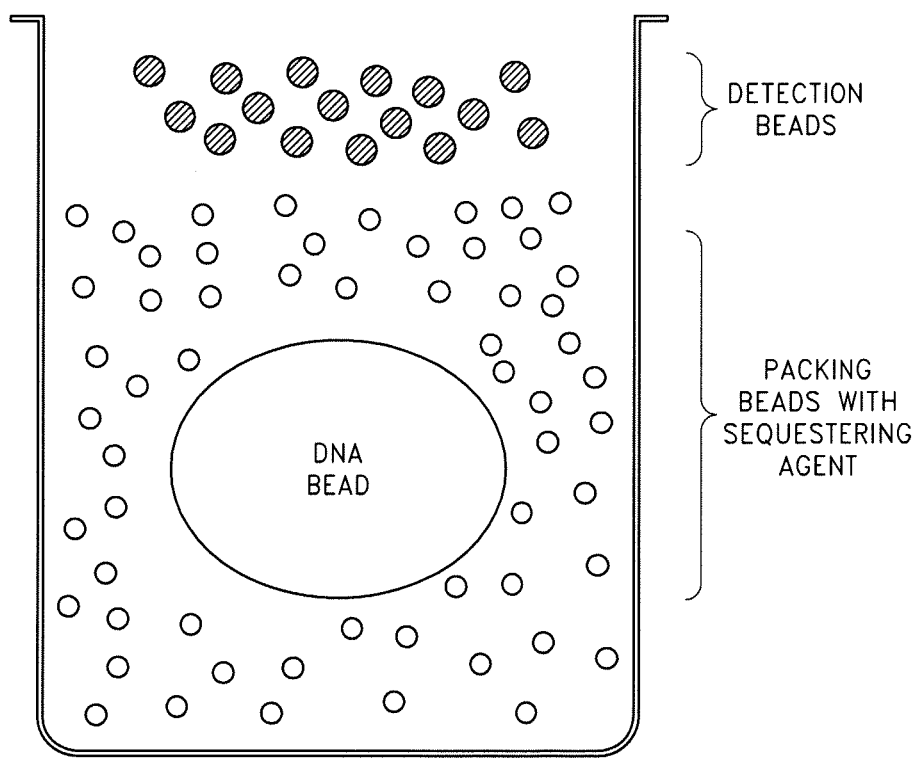

SEPARATION OF PYROPHOSPHATE RELEASE AND PYROPHOSPHATE DETECTION

CROSS-REFERENCE TO RELATED APPLICATIONS

This application is a U.S. National Phase of International Application No. PCT/US2010/025273, filed Feb. 24, 2010, designating the U.S. and published on Sep. 2, 2010 as WO 2010/099230, which claims priority under 35 U.S.C. § 119(e) to U.S. Provisional Application Ser. No. 61/155,424, filed Feb. 25, 2009, each of which is incorporated herein by reference in its entirety.

STATEMENT REGARDING FEDERALLY SPONSORED RESEARCH

This invention was made with Government support under NIH Grant Number 5R01HG003571-06 awarded by the Public Health Service (PHS). The Government has certain rights in the invention.

FIELD OF THE INVENTION

The present technology relates to molecular sciences, such as genomics. More particularly, the present technology relates to methods and systems for sequencing nucleic acids.

BACKGROUND

The detection of specific nucleic acid sequences present in a biological sample has a wide variety of applications, such as identifying and classifying microorganisms, diagnosing infectious diseases, detecting and characterizing genetic abnormalities, identifying genetic changes associated with cancer, studying genetic susceptibility to disease, and measuring response to various types of treatment. A valuable technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today one of the sequencing methodologies in use is pyrosequencing, which is based on the concept of sequencing-by-synthesis. The technique can be applied to massively parallel sequencing projects. For example, using an automated platform, it is possible to carry out hundreds of thousands of sequencing reactions simultaneously. Sequencing-by-synthesis differs from the classic dideoxy sequencing approach in that, instead of generating a large number of sequences and then characterizing them at a later step, real time monitoring of the incorporation of each base into a growing chain is employed. Although this approach is slow in the context of an individual sequencing reaction, it can be used for generating large amounts of sequence information in each cycle when hundreds of thousands to millions of reactions are performed in parallel. Despite these advantages, there are still limitations in the pyrosequencing approach.

SUMMARY

The present technology relates to methods and systems for detection of pyrophosphate, which can either be used alone or in connection with other technologies, such as pyrosequencing. In some embodiments of the present invention, such methods and systems permit the detection of pyrophosphate with reduced background. In some embodiments, methods and systems are described for pyrosequencing of nucleic acids with reduced background.

In some embodiments of the technology described herein, methods of delaying pyrophosphate detection are provided. The methods can include the steps of providing a pyrophosphate sequestering agent, generating pyrophosphate in the presence of the sequestering agent, whereby the pyrophosphate is reversibly sequestered, releasing the pyrophosphate from the sequestering agent and detecting the pyrophosphate.

In certain aspects, the pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent as exemplified herein. In certain aspects, the metal or metal oxide comprises Ti or $TiO_2$. In other aspects, the pyrophosphate sequestering agent comprises hydroxyapatite. In other aspects the sequestering agent comprises an ammonium or substituted ammonium salt, or a resin or bead that contains such groups. In certain aspects of the above embodiments, the pyrophosphate sequestering agent comprises particles or beads.

In certain aspects of the methods described herein, the step of releasing the pyrophosphate from the sequestering agent comprises providing a release reagent to the sequestering agent. In some aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects, the release reagent comprises phosphate. In other aspects the release reagent comprises a bisphosphonate. In certain aspects the release reagent is the enzyme ATP sulfurylase. In this particular aspect the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate.

In some methods described herein, the step of detecting the pyrophosphate comprises providing a pyrophosphate detecting agent. In certain aspects, the pyrophosphate detecting agent comprises luciferase. In certain aspects, the pyrophosphate detecting agent further comprises ATP sulfurylase. In certain aspects, the luciferase is attached to a bead. In certain aspects, the ATP sulfurylase is attached to a bead. In certain aspects, the ATP sulfurylase and the luciferase are both attached to the same bead.

In certain aspects of the above-described methods, the step of generating pyrophosphate in the presence of the sequestering agent comprises incorporating a nucleotide or nucleotide analog into a polynucleotide. In certain aspects, the polynucleotide is attached to a surface. In some aspects, the surface comprises a bead or a well. In certain aspects, the sequestering agent is disposed between the pyrophosphate detecting agent and the polynucleotide. Polynucleotides can comprise any type of nucleic acid but most often comprise DNA. In certain aspects, the DNA comprises genomic DNA and/or cDNA. Such genomic and/or cDNAs can include copies of genomic DNA sequences and/or cDNA sequences. Alternatively, the genomic DNA and/or cDNA can include fragments or copies of fragments of genomic DNA and/or cDNA sequences.

In certain aspects, the methods further comprise the step of washing the sequestering agent. In certain aspects, washing comprises adding a washing enzyme to the sequestering agent. In certain aspects, the washing enzyme is pyrophosphatase, apyrase, alkaline phosphatase and/or ATP sulfurylase. In certain aspects, the methods further comprise adding a washing enzyme inhibitor to the sequestering agent. In certain aspects, the washing enzyme inhibitor is sodium azide. In certain aspects, the washing step comprises electric-field assisted removal of pyrophosphate from the sequestering agent.

Also provided herein are methods for sequencing a nucleic acid. The method can include the steps of providing nucleotides or nucleotide analogs in the presence of a pyrophosphate sequestering agent and a pyrophosphate detecting agent, incorporating one or more of the nucleotides or nucleotide analogs into a polynucleotide so as to extend the polynucleotide in the presence of the pyrophosphate sequestering agent, thereby generating sequestered pyrophosphate, removing the unincorporated nucleotides or nucleotide analogs from the presence of the pyrophosphate detecting agent, releasing the pyrophosphate from the sequestering agent in the presence of the pyrophosphate detecting agent and detecting released pyrophosphate, wherein released pyrophosphate indicates that one or more nucleotides or nucleotide analogs have been incorporated into the polynucleotide.

In certain aspects, the pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or $TiO_2$. In other aspects, the pyrophosphate sequestering agent comprises hydroxyapatite. In other aspects the sequestering agent comprises an ammonium or substituted ammonium salt, or a resin or bead that contains such groups. In certain aspects of the above embodiments, the pyrophosphate sequestering agent comprises particles or beads.

In certain aspects, the step of releasing the pyrophosphate from the sequestering agent comprises providing a release reagent to the sequestering agent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects the release reagent comprises phosphate. In other aspects the release reagent comprises a bisphosphonate. In certain aspects the release reagent is the enzyme ATP sulfurylase. In this particular aspect, the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate.

In some of the sequencing methods described herein, the pyrophosphate detecting agent comprises luciferase. In certain aspects, the pyrophosphate detecting agent further comprises ATP sulfurylase. In certain aspects, the luciferase is attached to a bead. In certain aspects, the ATP sulfurylase is attached to a bead. In certain aspects, the ATP sulfurylase and the luciferase are both attached to the same bead.

In other aspects of the above-described methods, the polynucleotide is attached to a surface. In some aspects, the surface comprises a bead or a well. In certain aspects, the sequestering agent is disposed between the pyrophosphate detecting agent and the polynucleotide. Polynucleotides can comprise any type of nucleic acid but most often comprise DNA. In certain aspects, the DNA comprises genomic DNA and/or cDNA. Such genomic and/or cDNAs can include copies of genomic DNA sequences and/or cDNA sequences. Alternatively, the genomic DNA and/or cDNA can include fragments or copies of fragments of genomic DNA and/or cDNA sequences.

In some aspects, the sequencing methods further comprise the step of washing the sequestering agent. In some aspects, washing comprises adding a washing enzyme to the sequestering agent. In certain aspects, the washing enzyme is pyrophosphatase apyrase, alkaline phosphatase and/or ATP sulfurylase. In certain aspects, the methods further comprise adding a washing enzyme inhibitor to the sequestering agent. In some aspects, the washing enzyme inhibitor is sodium azide. In some aspects, the washing step comprises electric-field assisted removal of pyrophosphate from the sequestering agent.

In further aspects of the methods described herein, the removing step comprises washing the pyrophosphate detecting agent. In certain aspects, washing comprises adding a washing enzyme to the pyrophosphate detecting agent. In some aspects, the washing enzyme is a nucleotide degrading enzyme such as alkaline phosphatase or apyrase. In certain aspects, washing comprises electric-field assisted removal of pyrophosphate from the detecting agent.

Also provided herein are methods of modulating the availability of free pyrophosphate during sequencing of a nucleic acid molecule. These methods can include the steps of combining nucleotides or nucleotide analogs with a nucleic acid template; incubating the nucleic acid template and the nucleotides or nucleotide analogs together with a polymerase and a pyrophosphate sequestering agent under conditions sufficient to form a polynucleotide complementary to all or a portion of the nucleic acid template, wherein pyrophosphate generated during the incubating is reversibly sequestered by the sequestering agent, removing from the nucleic acid template the nucleotides or nucleotide analogs that have not been incorporated into the polynucleotide and releasing the pyrophosphate from the pyrophosphate sequestering agent by providing a release reagent.

In certain aspects, the pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or $TiO_2$. In other aspects, the pyrophosphate sequestering agent comprises hydroxyapatite. In other aspects the sequestering agent comprises an ammonium or substituted ammonium salt, or a resin or bead that contains such groups. In certain aspects of the above embodiments, the pyrophosphate sequestering agent comprises particles or beads.

In certain aspects, the step of releasing the pyrophosphate from the sequestering agent comprises providing a release reagent to the sequestering agent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects, the release reagent comprises phosphate. In other aspects, the release reagent comprises a bisphosphonate. In certain aspects, the release reagent is the enzyme ATP sulfurylase. In this particular aspect, the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate.

In some of the above-described methods, the pyrophosphate detecting agent comprises luciferase. In certain aspects, the pyrophosphate detecting agent further comprises ATP sulfurylase. In certain aspects, the luciferase is attached to a bead. In certain aspects, the ATP sulfurylase is attached to a bead. In certain aspects, the ATP sulfurylase and the luciferase are both attached to the same bead.

In other aspects of the above-described methods, the polynucleotide is attached to a surface. In some aspects, the surface comprises a bead or a well. In certain aspects, the sequestering agent is disposed between the pyrophosphate detecting agent and the polynucleotide. Polynucleotides can comprise any type of nucleic acid but most often comprise DNA. In certain aspects, the DNA comprises genomic DNA and/or cDNA. Such genomic and/or cDNAs can include copies of genomic DNA sequences and/or cDNA sequences. Alternatively, the genomic DNA and/or cDNA can include fragments or copies of fragments of genomic DNA and/or cDNA sequences.

In some aspects, the above-described methods further comprise the step of washing the sequestering agent. In some aspects, washing comprises adding a washing enzyme to the sequestering agent. In certain aspects, the washing enzyme is pyrophosphatase apyrase, alkaline phosphatase and/or ATP sulfurylase. In certain aspects, the methods further comprise adding a washing enzyme inhibitor to the sequestering agent. In some aspects, the washing enzyme inhibitor is sodium azide. In some aspects, the washing step comprises electric-field assisted removal of pyrophosphate from the sequestering agent.

In further aspects of the methods described herein, the removing step comprises washing the pyrophosphate detecting agent. In certain aspects, washing comprises adding a washing enzyme to the pyrophosphate detecting agent. In some aspects, the washing enzyme is a nucleotide degrading enzyme such as alkaline phosphatase or apyrase. In certain aspects, washing comprises electric-field assisted removal of pyrophosphate from the detecting agent.

Certain embodiments of the methods described above and elsewhere herein relate to sequestering pyrophosphate with a sequestering agent that involves a relatively weak interaction. In such embodiments, the unincorporated nucleotide triphosphates can be washed from the detection volume while the removal of pyrophosphate from the detection volume is retarded by the interaction of the pyrophosphate with the sequestering agent. In this regard, the method can function to permit separation of the nucleotide triphosphates from the pyrophosphate by permitting the nucleotide triphosphates to be eluted out of the detection volume before the pyrophosphate. In some aspects, the sequestering agent can function in ion-exchange, metal chelation or both. In such aspects, the release reagent can include, but is not limited to, substances that effect solvent composition, pH, concentration of ionic species and the like.

Also provided herein are arrays comprising a solid support having a plurality of sites distributed thereon, wherein at least a portion of the sites comprise a template nucleic acid and a pyrophosphate sequestering agent capable of reversibly sequestering pyrophosphate.

In certain aspects, the sites comprise wells. In certain aspects, the template nucleic acid is attached to a particle or bead within the wells.

In certain aspects, the wells further comprise beads having a pyrophosphate detecting agent attached thereto. In certain aspects, the pyrophosphate sequestering agent is disposed between the template nucleic acid and the pyrophosphate detecting agent. In certain aspects, the pyrophosphate detecting agent comprises ATP sulfurylase and luciferase. In certain aspects, the wells further comprise packing beads.

With respect to some embodiments of the arrays described herein, pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or $TiO_2$. In other aspects, the pyrophosphate sequestering agent comprises hydroxyapatite. In other aspects the sequestering agent comprises an ammonium or substituted ammonium salt, or a resin or bead that contains such groups. In certain aspects of the above embodiments, the pyrophosphate sequestering agent comprises particles or beads.

In addition to the foregoing, in some embodiments of the arrays described herein, pyrophosphate can be released from the sequestering agent by providing a release reagent to the sequestering agent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects the release reagent comprises phosphate. In other aspects the release reagent comprises a bisphosphonate. In certain aspects the release reagent is the enzyme ATP sulfurylase. In this particular aspect the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate.

In some aspects, arrays described herein can include sites that further comprise a polymerase and nucleotides or nucleotide analogs.

In certain aspects, arrays described herein can further comprises at least one electrode capable of producing an electric field in the presence of the sites.

Also provided herein are methods of making an array. The methods can include the steps of providing a solid support having a plurality of sites distributed thereon and providing a template nucleic acid and a pyrophosphate sequestering agent capable of reversibly sequestering pyrophosphate to at least a portion of the sites.

In certain aspects, the step of providing the template nucleic acid to the plurality of sites occurs prior to providing the pyrophosphate sequestering agent. In certain aspects, the step of providing the template nucleic acid to the plurality of sites occurs subsequent to providing the pyrophosphate sequestering agent. In certain aspects, the step of providing the template nucleic acid to the plurality of sites occurs at the same time as providing the pyrophosphate sequestering agent.

In certain aspects, the sites comprise wells. In certain aspects, a reagent useful in the methods is attached to a bead. For example, a template nucleic acid, pyrophosphate sequestering agent or pyrophosphate detecting agent can be attached to a particle or bead. In certain aspects the beads are provided to wells by packing, for example, via centrifugation.

In certain aspects, the methods further comprise the step of providing to the wells beads having a pyrophosphate detecting agent attached thereto. In certain aspects, the pyrophosphate detecting agent comprises ATP sulfurylase and luciferase. In certain aspects, the step of providing said beads having a pyrophosphate detecting agent to the wells occurs prior to providing the pyrophosphate sequestering agent. In certain aspects, the step of providing said beads having a pyrophosphate detecting agent to the wells occurs subsequent to providing the pyrophosphate sequestering agent. In certain aspects, the step of providing said beads having a pyrophosphate detecting agent to the wells occurs at the same time as providing the pyrophosphate sequestering agent.

In certain aspects, the methods further comprise the step of providing packing beads to the wells. In certain aspects, the beads having a pyrophosphate detecting agent attached thereto and the packing beads are provided to the wells at the same time.

In certain aspects, the methods further comprise the step of providing a polymerase and nucleotides or nucleotide analogs to the sites.

In certain aspects of the above-described methods of making an array, the step of providing comprises applying a voltage to the plurality of sites.

Arrays manufactured according to the methods described herein can be employed in the sequencing and/or pyrophosphate sequestering and release processes described above and elsewhere herein. For example, in some embodiments, the pyrophosphate is reversibly sequestered by adsorption with the sequestering agent. In certain aspects, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or $TiO_2$. In other aspects, the pyrophosphate sequestering agent comprises hydroxyapatite. In other aspects the sequestering agent comprises an ammonium or substituted ammonium salt, or a resin or bead that contains such groups. In certain aspects of the above embodiments, the pyrophosphate sequestering agent comprises particles or beads.

In addition to the foregoing, in some embodiments, arrays manufactured according to the methods described herein can be utilized in processes in which pyrophosphate can be released from the sequestering agent by providing a release reagent to the sequestering agent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N, N',N'-tetra-acetic acid (EGTA) citric acid, tartaric acid, acetic or other carboxylic acids or their salts. In other aspects the release reagent comprises phosphate. In other aspects the release reagent comprises a bisphosphonate. In certain aspects the release reagent is the enzyme ATP sulfurylase. In this particular aspect the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). Typically, the ATP will have a lower binding affinity for the sequestering agent than does pyrophosphate.

BRIEF DESCRIPTION OF THE DRAWINGS

FIG. 1 shows a schematic of a well packed with beads according to one embodiment.

DETAILED DESCRIPTION

Pyrophosphate anion (hereinafter "PPi") participates in several bioenergetic and metabolic processes, such as the synthesis of cyclic AMP as a second messenger from ATP with the concomitant release of PPi. PPi is released during a polymerase reaction upon incorporation of a dNTP into a polynucleotide. As discussed further below, the release of pyrophosphate during nucleotide incorporation has been exploited as a means for signaling nucleotide incorporation during sequencing processes.

The pyrophosphate-based nucleic acid sequencing method (herein below referred to as pyrosequencing) has been described by Ronaghi et al. (see, for example, U.S. Pat. No. 6,210,891; and Ronaghi et al. (1998). A sequencing method based on real-time pyrophosphate. *Science* 281:363-365, the disclosures of which are incorporated herein by reference in their entireties). This technique is based on the observation that PPi can be detected by a number of assays. In a polymerase reaction, a sequencing primer is annealed to the template. If a nucleotide complements the next base in the template (i.e. next correct base 3' of the primer sequence), it is incorporated into the growing primer chain, and PPi is released. When only one of the four nucleotides is introduced into the reaction at a time, PPi is generated only when the correct nucleotide is introduced. Thus, the production of PPi reveals the identity of the next correct base. In this way, a sequence from a template is obtained or confirmed. Additional nucleotides of the sequence can be obtained by cycling of the polymerase reaction, in the presence of a single nucleotide at a time.

As used herein, "nucleic acid polymerase" or "polymerase" refers to an enzyme that catalyzes the polymerization of nucleoside triphosphates. Polymerases include, but are not limited to, DNA polymerases, RNA polymerases, reverse transcriptases and the like. Generally, the enzyme will initiate synthesis at the 3'-end of the primer annealed to a template sequence, and will continue synthesis moving toward the 5'-end of the template, and if possessing a 5' to 3' nuclease activity, it may hydrolyze intervening, annealed probe to release both labeled and unlabeled probe fragments, until synthesis terminates.

As used herein, the term "DNA polymerase" refers to an enzyme which catalyzes the synthesis of DNA. It uses one strand of the DNA duplex as a template. For example, templates may include, but are not limited to, single-stranded DNA, partially duplexed DNA and nicked double-stranded DNA. The polymerase can generate a new strand from primers hybridized to the template. As presented herein, an oligonucleotide primer can be used which has a free 3'-OH group. The polymerase then copies the template in the 5' to 3' direction provided that sufficient quantities of free nucleotides, such as dATP, dGTP, dCTP, 5-methyl dCTP or dTTP are present. Examples of DNA polymerases include, but are not limited to, *E. coli* DNA polymerase I, the large proteolytic fragment of *E. coli* DNA polymerase I, commonly known as "Klenow" polymerase, "Taq" polymerase, T7 polymerase, Bst DNA polymerase, T4 polymerase, T5 polymerase, reverse transcriptase, exo-BCA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (PfU) DNA polymerase. DNA polymerases that lack exonuclease activity, either by mutation or otherwise, are often referred to as exo minus polymerases and are also useful in particular embodiments of the invention.

As used herein, "a portion," "at least a portion" and grammatical equivalents thereof can refer to any fraction of a whole amount. In some embodiments, "at least a portion" refers to at least about 10%, 20%, 30%, 40%, 50%, 60%, 70%, 80%, 90% and 100% of a whole amount.

There are several methods that can be used to detect PPi. One such assay uses two enzymes, ATP-sulfurylase and luciferase, to produce a light emission. ATP-sulfurylase generates ATP in the presence of PPi and adenosine-5'-phosphosulfate (APS). Luciferase uses the ATP produced by the reaction of PPi and APS to convert luciferin to oxyluciferin, emitting a photon. One problem of this reaction is that luciferase is not absolutely specific for ATP, it can also utilize dATP, and to a lesser extent may catalyze reaction with other nucleoside triphosphates as well. As such, the background can be high and non-specific reactions can happen, particularly when using dATP. Accordingly, there remains a need for methods and systems which facilitate, or otherwise improve, the detection of PPi.

As described herein, systems and methods have been developed to reduce the background associated with pyrophosphate detection during sequencing. In some embodiments, the systems and methods described herein for reversibly sequestering PPi profoundly reduce background signal and increases sequence read length. Thus, one embodiment provided herein is a method of delaying pyrophosphate detection until after at least a portion of background producing and/or interfering substances have be removed from the area of detection. Exemplary substances that can be removed prior to release and detection of pyrophosphate include, but are not limited to polymerase, nucleotides, template nucleic acids pr primer nucleic acids.

In some embodiments, the method can include the steps of providing a pyrophosphate sequestering agent, generating pyrophosphate in the presence of the sequestering agent, whereby the pyrophosphate is reversibly sequestered, releasing the pyrophosphate from the sequestering agent and detecting the pyrophosphate. The releasing can be due to a change in conditions, such as addition of a release reagent. However, the releasing can also occur due to natural dissociation between the pyrophosphate and sequestering agent. As such, release of pyrophosphate from a reversible sequestering agent need not require addition of a release reagent or any other change in binding conditions. Accordingly, reversible sequestering of pyrophosphate can have the effect of retarding diffusion of pyrophosphate and the degree to which diffusion is retarded can be a function of the rates of binding and dissociation between pyrophosphate and the sequestering agent. Sequestering and retardation of diffusion in the methods set forth herein can be characterized in terms of binding rate constant, dissociation rate constant and/or equilibrium binding constants in accordance with chromatographic theory.

Also provided herein is a method for sequencing all or a portion of a nucleic acid. The method can include the steps of providing nucleotides or nucleotide analogs in the presence of a pyrophosphate sequestering agent and a pyrophosphate detecting agent, incorporating one or more of the nucleotides or nucleotide analogs into a polynucleotide so as to extend the polynucleotide in the presence of the pyrophosphate sequestering agent, thereby generating sequestered pyrophosphate, removing the unincorporated nucleotides or nucleotide analogs from the presence of the pyrophosphate detecting agent, releasing the pyrophosphate from the sequestering agent in the presence of the pyrophosphate detecting agent and detecting released pyrophosphate, wherein released pyrophosphate indicates that one or more nucleotides or nucleotide analogs have been incorporated into the polynucleotide.

Also provided herein is a method of modulating the availability of free pyrophosphate during sequencing of a nucleic acid molecule. The method can include the steps of combining nucleotides or nucleotide analogs with a nucleic acid template, incubating the nucleic acid template and the nucleotides or nucleotide analogs together with a polymerase and a pyrophosphate sequestering agent under conditions sufficient to form a polynucleotide complementary to all or a portion of the nucleic acid template, wherein pyrophosphate generated during the incubating is reversibly sequestered by the sequestering agent, removing from the nucleic acid template the nucleotides or nucleotide analogs that have not been incorporated into the polynucleotide and releasing the pyrophosphate from the pyrophosphate sequestering agent by providing a release reagent.

Also provided herein is an array comprising a solid support having a plurality of sites distributed thereon, wherein at least a portion of the sites comprise a template nucleic acid and a pyrophosphate sequestering agent capable of reversibly sequestering pyrophosphate.

Also provided herein is a method of making an array. The method can include the steps of providing a solid support having a plurality of sites distributed thereon and providing a template nucleic acid and a pyrophosphate sequestering agent capable of reversibly sequestering pyrophosphate to at least a portion of the sites.

Sequestering of Pyrophosphate

Sequestering PPi allows other background-causing and/or interfering factors to be removed from a detection system. Accordingly, the methods and systems provided herein can create a means for temporal and spatial control of PPi detection. The timing of PPi detection can thus be controlled to improve any number of factors that influence the quality and/or quantity of signals, including background signal.

In accordance with the foregoing, methods of delaying pyrophosphate detection are described herein. For example, in some embodiments, the method can include the steps of providing a pyrophosphate sequestering agent, generating pyrophosphate in the presence of the sequestering agent, whereby the pyrophosphate is reversibly sequestered, releasing the pyrophosphate from the sequestering agent and then detecting the pyrophosphate.

As used herein, generating PPi can include any chemical, physical or biological process which produces PPi. Although many of the methods and compositions disclosed herein are exemplified or described in connection with nucleic acid sequencing, it will be appreciated that these methods and compositions can be used with other systems or processes where detection of PPi is performed or desired. For example, such methods find application in biological reactions catalyzed by fatty acyl-CoA synthetase, which generate PPi as a byproduct. Such methods can also be applied in the detection of metabolic processes, such as the synthesis of cyclic AMP as a second messenger from ATP, which results in the release of PPi.

Accordingly, in some of the above-described methods, the step of generating pyrophosphate in the presence of the sequestering agent comprises incorporating a nucleotide or nucleotide analog into a polynucleotide. In certain aspects, the polynucleotide is attached to a surface. In some embodiments, the surface can comprise a bead or a well. In certain aspects, the sequestering agent is disposed between the pyrophosphate detecting agent and the polynucleotide.

It will be appreciated that the polynucleotides described herein can comprise essentially any type of nucleic acid. In some embodiments of the present systems and methods described herein, the polynucleotides comprise DNA. The DNA utilized herein is not limited by type but most often comprises genomic DNA (gDNA) or cDNA. Genomic DNA can refer to actual nucleic acid material isolated from an organism, or alternatively, one or more copies of portions of the genome of an organism or one or more copies of the entire genome of an organism. For example, genomic DNA can refer to a copy of a fragment of genomic DNA that has been isolated from an organism. In some embodiments, genomic DNA is isolated from a cell or other material and fragmented. The fragments are then copied or otherwise amplified. Although this amplified material may contain replica sequences rather than nucleic acid molecules isolated directly from the organism, this material is still referred to herein as genomic DNA or DNA obtained from the genome of an organism. As such, the genomic DNA described herein can include fragments or copies of fragments of genomic DNA sequences.

As used herein, a pyrophosphate sequestering agent is any agent that is capable of absorbing, chelating, binding or forming a chemical bond or complex with PPi, so as to render the PPi substantially incapable of chemically reacting with other surrounding materials. The term reversibly sequestered indicates that PPi is capable of being removed, dissociated, released or desorbed from the sequestering agent. Typically, the pyrophosphate is reversibly sequestered by adsorption with or onto the sequestering agent. Accordingly, any suitable sequestering agent can be used in the methods and systems provided herein. Useful pyrophosphate sequestering agents can have one or more of the following properties: having cationic charge, being a divalent cation, being capable of binding pyrophosphate via chelation, being a metal cation, being an alkaline earth or a transition metal, and being capable of tetravalent complexation. For example, in certain aspects, the sequestering agent comprises a cationic agent. Many cationic agents known in the art are useful. Some examples include salts and oxides of metals such as aluminum, alkaline earth metals and salts and oxides thereof, such as those of calcium, magnesium or strontium, in particular calcium phosphates such as hydroxyapatite. Transition metals and transition metal oxides can be particularly useful. For example, in certain aspects, the metal or metal oxide comprises a tetravalent metal such as titanium (Ti) or titanium dioxide ($TiO_2$). The metal salt can be soluble, such as a metal chloride. In this aspect, it is desirable that the metal cation of this salt forms an insoluble salt when the anion of the soluble salt is displaced by pyrophosphate, or the pyrophosphate forms additional coordination to the metal cation. Other examples of useful transition metals include but are not limited to zirconium, vanadium, molybdenum, manganese, iron, cobalt, nickel, copper, zinc, and cadmium.

In other aspects, the cationic agent comprises hydroxyapatite, a pyridinium salt, a substituted pyridinium salt, a quaternary ammonium salt, a polymer bound substituted ammonium, or a polymer bound pyridinium salt. In certain aspects of the above embodiments, the pyrophosphate sequestering agent comprises particles or beads. For example, the sequestering agent can be deposited onto the surface of a bead or particle. In some embodiments, the inner surface of porous beads can be coated with a sequestering agent. Alternatively, the bead or particle can be composed of, or otherwise comprise, the sequestering agent.

In other aspects of the systems and methods described herein, the sequestering agent can be an anion exchange resin containing positively charged groups such as, ammonium, alkylamonium, pyridinium ions, or the like. The sequestering agent can include ammonium, substituted ammonium or pyridinium salts, or the like. In other aspects the sequestering agent includes a mixed salt of metals and ammonium or substituted ammonium salts. Particularly useful sequestering agents have a high affinity for binding pyrophosphate. Useful sequestering agents will also typically be selective for pyrophosphate, for example, have a higher affinity for pyrophosphate than for nucleotide or deoxynucleotide triphosphates or other reagents and products that occur in a sequencing-by-synthesis reaction.

A zeolite or molecular sieve can also be useful as a pyrophosphate sequestering agent. Zeolite molecular sieves are crystalline, highly porous materials, which belong to the class of aluminosilicates. These crystals are characterized by a three-dimensional pore system, with pores of precisely defined diameter. The corresponding crystallographic structure is formed by tetrahedras of ($AlO_4$) and ($SiO_4$). The ability to adjust the pores to desired uniform openings allows for molecules smaller than its pore diameter to be adsorbed whilst excluding larger molecules, hence the name "molecular sieve". As such, a zeolite can be used that is capable of adsorbing pyrophosphate while excluding larger molecules that are present in a pyrosequencing reaction such as nucleotides, nucleotide analogs, nucleic acids, enzymes and the like.

In certain aspects of the methods described herein, the step of releasing the pyrophosphate from the sequestering agent comprises providing a release reagent to the sequestering agent. Release reagents of the present embodiments are described in greater detail below.

In some methods described herein, the step of detecting the pyrophosphate comprises providing a pyrophosphate detecting agent. As described in greater detail below, the pyrophosphate detecting agent can be any compound, agent or enzyme used to indicate the presence of pyrophosphate.

Methods of Sequencing

Also provided herein is a method for sequencing a nucleic acid. The method can include the steps of providing nucleotides or nucleotide analogs in the presence of a pyrophosphate sequestering agent and a pyrophosphate detecting agent incorporating one or more of the nucleotides or nucleotide analogs into a polynucleotide so as to extend the polynucleotide in the presence of the pyrophosphate sequestering agent, thereby generating sequestered pyrophosphate; removing the unincorporated nucleotides or nucleotide analogs from the presence of the pyrophosphate detecting agent, releasing the pyrophosphate from the sequestering agent in the presence of the pyrophosphate detecting agent and detecting released pyrophosphate, wherein released pyrophosphate indicates that one or more nucleotides or nucleotide analogs have been incorporated into the polynucleotide.

Also provided herein is a method of modulating the availability of free pyrophosphate during sequencing of a nucleic acid molecule. The method can include the steps of combining nucleotides or nucleotide analogs with a nucleic acid template, incubating the nucleic acid template and the nucleotides or nucleotide analogs together with a polymerase and a pyrophosphate sequestering agent under conditions sufficient to form a polynucleotide complementary to all or a portion of the nucleic acid template, wherein pyrophosphate generated during the incubating is reversibly sequestered by the sequestering agent, removing from the nucleic acid template the nucleotides or nucleotide analogs that have not been incorporated into the polynucleotide, and releasing the pyrophosphate from the pyrophosphate sequestering agent by providing a release reagent. In certain aspects, the method further comprises the step of providing a pyrophosphate detecting agent, thereby detecting pyrophosphate that is released from the pyrophosphate sequestering agent. In certain aspects, the step of releasing the pyrophosphate from the sequestering agent comprises providing a release reagent to the sequestering agent, as described in greater detail hereinbelow.

In some sequencing by synthesis methodologies, incorporation of a dNTP into a polynucleotide is determined by assaying for the presence of a reaction byproduct. In pyrosequencing, the nucleotide sequence of the polynucleotide sequencing product can be determined by measuring inorganic pyrophosphate (PPi) liberated from a deoxynucleotide triphosphate (dNTP) as the dNTP is incorporated into an extended sequence primer. Such pyrosequencing methods can be performed in solution (liquid phase) or as a solid phase technique. PPi-based sequencing methods are described generally in, e.g., WO9813523A1, Ronaghi, et al., 1996. Anal. Biochem. 242: 84-89, Ronaghi, et al., 1998. Science 281: 363-365 (1998), U.S. Pat. Nos. 6,210,891; 6,258,568 and 6,274,320. These disclosures of PPi-based sequencing are incorporated herein by reference in their entireties.

Pyrophosphate released during the synthesis reaction can be detected enzymatically (e.g., by the generation of light in the luciferase-luciferin reaction). Such methods enable a nucleotide to be identified in a given target position, and the DNA to be sequenced simply and rapidly while avoiding the need for electrophoresis and the use of potentially dangerous radiolabels.

PPi can be detected by a number of different methodologies, and various enzymatic methods have been previously described (see e.g., Reeves, et al., 1969. Anal. Biochem. 28: 282-287; Guillory, et al., 1971. Anal. Biochem. 39: 170-180; Johnson, et al., 1968. Anal. Biochem. 15: 273; Cook, et al., 1978. Anal. Biochem. 91: 557-565; and Drake, et al., 1979. Anal. Biochem. 94: 117-120). In pyrosequencing PPi can be detected by first converting it to ATP using APS and ATP-sulfurylase. The ATP can then be used as a substrate for the light-producing enzyme, luciferase.

ATP-Sulfurylase

PPi liberated as a result of incorporation of a dNTP by a polymerase can be converted to ATP using, e.g., an ATP sulfurylase. This enzyme has been identified as being involved in sulfur metabolism. Sulfur, in both reduced and oxidized forms, is an essential mineral nutrient for plant and animal growth (see e.g., Schmidt and Jager, 1992. Ann. Rev. Plant Physiol. Plant Mol. Biol. 43: 325-349). In both plants and microorganisms, active uptake of sulfate is followed by reduction to sulfide. As sulfate has a very low oxidation/reduction potential relative to available cellular reductants, the primary step in assimilation requires its activation via an ATP-dependent reaction (see e.g., Leyh, 1993. Crit. Rev. Biochem. Mol. Biol. 28: 515-542). ATP sulfurylase (ATP: sulfate adenylyltransferase; EG 2.7.7.4) catalyzes the initial reaction in the metabolism of inorganic sulfate ($SO_4^{-2}$); see e.g., Robbins and Lipmann, 1958. J. Biol. Chem. 233: 686-690; Hawes and Nicholas, 1973. Biochem. J. 133: 541-550). In this reaction $SO_4^{-2}$ is activated to adenosine 5'-phophosulfate (APS).

ATP sulfurylase has been highly purified from several sources, such as *Saccharomyces cerevisiae* (see e.g., Hawes and Nicholas, 1973. Biochem. J. 133: 541-550); *Penicillium chrysogenum* (see e.g., Renosto, et al., 1990. J. Biol. Chem. 265: 10300-10308); rat liver (see e.g., Yu, et al., 1989. Arch. Biochem. Biophys. 269: 165-174); and plants (see e.g., Shaw and Anderson, 1972. Biochem. J. 127: 237-247; Osslund, et al., 1982. Plant Physiol. 70: 39-45). Furthermore, ATP sulfurylase genes have been cloned from prokaryotes (see e.g., Leyh, et al., 1992. J. Biol. Chem. 267: 10405-10410; Schwedock and Long, 1989. Mol. Plant. Microbe Interaction 2: 181-194; Laue and Nelson, 1994. J. Bacteriol. 176: 3723-3729); eukaryotes (see e.g., Cherest, et al., 1987. Mol. Gen. Genet. 210: 307-313; Mountain and Korch, 1991. Yeast 7: 873-880; Foster, et al., 1994. J. Biol. Chem. 269: 19777-19786); plants (see e.g., Leustek, et al., 1994. Plant Physiol. 105: 897-90216); and animals (see e.g., Li, et al., 1995. J. Biol. Chem. 270: 29453-29459). The enzyme is homo-oligomer or heterodimer, depending upon the specific source (see e.g., Leyh and Suo, 1992. J. Biol. Chem. 267: 542-545).

ATP-sulfurylase has been used for many different applications, for example, bioluminometric detection of ADP at high concentrations of ATP (see e.g., Schultz, et al., 1993. Anal. Biochem. 215: 302-304); continuous monitoring of DNA polymerase activity (see e.g., Nyrbn, 1987. Anal. Biochem. 167: 235-238); and DNA sequencing (see e.g., Ronaghi, et al., 1996. Anal. Biochem. 242: 84-89; Ronaghi, et al., 1998. Science 281: 363-365; Ronaghi, et al., 1998. Anal. Biochem. 267: 65-71).

Several assays have been developed for detection of the forward ATP-sulfurylase reaction. The colorimetric molybdolysis assay is based on phosphate detection (see e.g., Wilson and Bandurski, 1958. J. Biol. Chem. 233: 975-981), whereas the continuous spectrophotometric molybdolysis assay is based upon the detection of NADH oxidation (see e.g., Seubert, et al., 1983. Arch. Biochem. Biophys. 225: 679-691; Seubert, et al., 1985. Arch. Biochem. Biophys. 240: 509-523). The latter assay requires the presence of several detection enzymes. In addition, several radioactive assays have also been described in the literature (see e.g., Daley, et al., 1986. Anal. Biochem. 157: 385-395). For example, one assay is based upon the detection of $^{32}$PPi released from $^{32}$P-labeled ATP (see e.g., Seubert, et al., 1985. Arch. Biochem. Biophys. 240: 509-523) and another on the incorporation of $^{35}S$ into $[^{35}S]$-labeled APS (this assay also requires purified APS kinase as a coupling enzyme; see e.g., Seubert, et al., 1983. Arch. Biochem. Biophys. 225: 679-691); and a third reaction depends upon the release of $^{35}SO_4^{-2}$ from $[^{35}S]$-labeled APS (see e.g., Daley, et al., 1986. Anal. Biochem. 157: 385-395).

For detection of the reversed ATP sulfurylase reaction a continuous spectrophotometric assay (see e.g., Segel, et al., 1987. Methods Enzymol. 143: 334-349); a bioluminometric assay (see e.g., Balharry and Nicholas, 1971. Anal. Biochem. 40: 1-17); an $^{35}SO_4^{-2}$ release assay (see e.g., Seubert, et al, 1985. Arch. Biochem. Biophys. 240: 509-523); and a .sup.32 PPi incorporation assay (see e.g., Osslund, et al., 1982. Plant Physiol. 70: 39-45) have been previously described.

Luciferase Enzymes

ATP produced by an ATP sulfurylase can be converted using enzymatic reactions which convert ATP to light. Light-emitting chemical reactions (i.e., chemiluminescence) and biological reactions (i.e., bioluminescence) are useful in analytical biochemistry for sensitive measurements of various metabolites. In bioluminescent reactions, the chemical reaction that leads to the emission of light is enzyme-catalyzed. For example, the luciferin-luciferase system allows for specific assay of ATP and the bacterial luciferase-oxidoreductase system can be used for monitoring of NAD(P)H. Both systems have been extended to the analysis of numerous substances by means of coupled reactions involving the production or utilization of ATP or NAD(P)H (see e.g., Kricka, 1991. Chemiluminescent and bioluminescent techniques. Clin. Chem. 37: 1472-1281).

The development of new reagents has made it possible to obtain stable light emission proportional to the concentrations of ATP (see e.g., Lundin, 1982. Applications of firefly luciferase In; Luminescent Assays (Raven Press, New York) or NAD(P)H (see e.g., Lovgren, et al., Continuous monitoring of NADH-converting reactions by bacterial luminescence. J. Appl. Biochem. 4: 103-111). With such stable light emission reagent, it is possible to make endpoint assays and to calibrate each individual assay by addition of a known amount of ATP or NAD(P)H. In addition, a stable light-emitting system also allows continuous monitoring of ATP- or NAD(P)H-converting systems.

Suitable enzymes for converting ATP into light include luciferases, e.g., insect luciferases. Luciferases produce light as an end-product of catalysis. The best known light-emitting enzyme is that of the firefly, *Photinus pyralis* (Coleoptera). The corresponding gene has been cloned and expressed in bacteria (see e.g., de Wet, et al., 1985. Proc. Natl. Acad. Sci. USA 80: 7870-7873) and plants (see e.g., Ow, et al., 1986. Science 234: 856-859), as well as in insect (see e.g., Jha, et al., 1990. FEBS Lett. 274: 24-26) and mammalian cells (see e.g., de Wet, et al., 1987. Mol. Cell. Biol. 7: 725-7373; Keller, et al., 1987. Proc. Natl. Acad. Sci. USA 82: 3264-3268). In addition, a number of luciferase genes from the Jamaican click beetle, *Pyroplorus plagiophihalamus* (Coleoptera), have been cloned and partially characterized (see e.g., Wood, et al., 1989. J. Biolumin. Chemilumin. 4: 289-301; Wood, et al., 1989. Science 244: 700-702). Distinct luciferases can sometimes produce light of different wavelengths, which may enable simultaneous monitoring of light emissions at different wavelengths. Accordingly, these aforementioned characteristics are unique, and add new dimensions with respect to the utilization of current reporter systems.

Firefly luciferase catalyzes bioluminescence in the presence of luciferin, adenosine 5'-triphosphate (ATP), magnesium ions, and oxygen, resulting in a quantum yield of 0.88 (see e.g., McElroy and Selinger, 1960. Arch. Biochem. Biophys. 88: 136-145). The firefly luciferase bioluminescent reaction can be utilized as an assay for the detection of ATP with a detection limit of approximately $1 \times 10^{-13}$ M (see e.g., Leach, 1981. J. Appl. Biochem. 3: 473-517). In addition, the overall degree of sensitivity and convenience of the luciferase-mediated detection systems have created considerable interest in the development of firefly luciferase-based biosensors (see e.g., Green and Kricka, 1984. Talanta 31: 173-176; Blum, et al., 1989. J. Biolumin. Chemilumin. 4: 543-550).

In accordance with the above, in some methods described herein, the pyrophosphate detecting agent comprises luciferase. In certain aspects, the pyrophosphate detecting agent further comprises ATP-sulfurylase. The ATP-sulfurylase and/or luciferase can either be free or attached to a substrate. In some embodiments, the ATP-sulfurylase and/or luciferase are attached, or otherwise coupled, to a surface of a substrate, for example, a surface of an array substrate. In some embodiments, the array substrate can comprise one or more depressions or wells and the ATP-sulfurylase and/or luciferase can be attached, or otherwise coupled, to the a surface of the one or more depressions or wells. In certain aspects, the luciferase is attached to a bead. In certain aspects, the ATP-sulfurylase is attached to a bead. In certain aspects, the ATP-sulfurylase and the luciferase are both attached to the same bead. Alternatively, the ATP-sulfurylase and luciferase can be attached to separate beads. In preferred embodiments the beads can reside within depressions or wells of an array substrate.

Release Reagents

In some embodiments provided herein, PPi which has been reversibly sequestered can be released into solution by a release reagent. In some embodiments, the release reagent is a chelating agent. In some preferred embodiments, the step of releasing the pyrophosphate from the sequestering agent comprises providing a release reagent to the sequestering agent. In certain embodiments, the release reagent comprises an anion capable of displacing the pyrophosphate from the sequestering agent, for example, by preferentially complexing or chelating the cation of the sequestering agent. In some embodiments, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects the release reagent comprises phosphate. In other embodiments, the release reagent can comprise a bisphosphonate. In some embodiments, the release reagent is the enzyme ATP sulfurylase. In some of these embodiments, the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). The ATP has a lower binding affinity for the sequestering agent than does pyrophosphate.

Pyrosequencing Embodiments

Using the above-described enzymes, the nucleic acid to be sequenced and a primer sequence can be exposed to a polymerase and a known dNTP. If the dNTP is incorporated onto the 3' end of the primer sequence, the dNTP is cleaved and a PPi molecule is liberated. The PPi is then converted to ATP with ATP-sulfurylase. Preferably, the ATP-sulfurylase is present at a sufficiently high concentration that the conversion of PPi proceeds with first-order kinetics. In the presence of luciferase, the ATP is hydrolyzed to liberate a photon. The reaction preferably has a sufficient concentration of luciferase present within the reaction mixture such that the reaction proceeds with first-order kinetics. The photon can be measured using methods and apparatuses described below.

For most applications it is desirable to wash away diffusible sequencing reagents, e.g., unincorporated dNTPs, with a wash buffer. Any wash buffer used in pyrophosphate sequencing can be used. An example of a wash buffer is 10 mM Trisc-HCl (pH 7.5), 1 mM EDTA, 2 M NaCl, 1% Tween 20 (Nyren et al., Anal. Biochem. 208:171-75, 1993).

In some embodiments, the concentration of reactants in the sequencing reaction include 1 pmol DNA, 3 pmol polymerase, 40 pmol dNTP in 0.2 ml buffer. See Ronaghi, et al., Anal. Biochem. 242: 84-89 (1996).

The sequencing reaction can be performed with each of four predetermined nucleotides, if desired. A "complete" cycle generally includes sequentially administering sequencing reagents for each of the nucleotides dATP, dGTP, dCTP and dTTP (or dUTP), in a predetermined order. Pyrophosphate is typically detected between each of the nucleotide additions. Unincorporated dNTPs can be washed away between each of the nucleotide additions. Alternatively or additionally, unincorporated dNTPs can be degraded by apyrase (see below) or alkaline phosphatase. The wash buffer can contain an additive that helps to release nucleotide triphosphates, in particular dATP and dATP analogs, that bind to the luciferase enzyme. In certain instances this additive can be an inhibitor of luciferase. The cycle can be repeated as desired until the desired amount of sequence of the sequence product is obtained. In some embodiments, about 10-10,000, about 10-1000, about 10-100, about 10-75, about 20-50, or about 30 nucleotides of sequence information is obtained from one annealed primer. In preferred embodiments, the sequencing information exceeds 200 nucleotides of sequence. In more preferred embodiments, the sequencing information exceeds 500 nucleotides of sequence. In even more preferred embodiments, the sequencing information exceeds 1000 nucleotides of sequence.

Although luciferase prefers to use ATP as a substrate, this enzyme can also hydrolyze dATP directly with concomitant release of a photon. Such hydrolysis results in a false positive signal because the hydrolysis occurs independent of incorporation of the dATP into the growing polynucleotide. To avoid this problem, dATP analogs have been developed, which can be incorporated into DNA using a DNA polymerase but are not efficient substrates for luciferase. One such analog is α-thio-dATP.

Typically, the PPi-based detection is calibrated by the measurement of the light released following the addition of control nucleotides to the sequencing reaction mixture immediately after the addition of the sequencing primer. This allows for normalization of the reaction conditions. Incorporation of two or more identical nucleotides in succession is revealed by a corresponding increase in the amount of light released. Thus, a two-fold increase in released light relative to control nucleotides reveals the incorporation of two successive dNTPs into the extended primer.

If desired, apyrase may be "washed" or "flowed" over the surface of the solid support so as to facilitate the degradation of any remaining, non-incorporated dNTPs within the sequencing reaction mixture. As used herein, "apyrase" refers to an enzyme that catalyses the hydrolysis of NTP to yield NMP and inorganic phosphate. Apyrase can also act on NDP and other nucleoside triphosphates and diphosphates with the general reaction being NTP->NDP+Pi->NMP+2Pi. Accordingly, upon treatment with apyrase, any remaining reactants are washed away in preparation for the following dNTP incubation and photon detection steps. Alternatively, the apyrase may be bound to the solid support. Alkaline phosphatase can be used in a similar way.

When the support is planar, the pyrophosphate sequencing reactions preferably take place in a thin, aqueous reaction chamber comprising an optically-transparent solid support surface and an optically-transparent cover. Sequencing reagents may then be delivered by flowing them across the surface of the substrate. When the support is not planar, the reagents may be delivered by dipping the solid support into baths of any given reagents.

In some embodiments, the enzymes utilized in the pyrophosphate sequencing reaction (e.g., sulfurylase, luciferase, and apyrase) may be attached to, or otherwise coupled to, the solid support. When luciferase is attached or otherwise coupled to the solid support, it is often present less than 50 μm from an anchored primer. However, in certain embodiments described herein, the luciferase can be located much further from the site of nucleotide incorporation. In embodiments wherein the luciferase is physically separated from the site of nucleotide incorporation, a sequestering agent can be physically located in the space intervening between the luciferase and site of nucleotide incorporation.

The photons generated by luciferase may be quantitated using a variety of detection apparatuses, e.g., a photomultiplier tube, charge-coupled device (CCD), absorbance photometer, and a luminometer, as well as the apparatuses described herein. In a preferred embodiment, the quantitation of the emitted photons is accomplished by the use of charge-coupled display (CCD) camera fitted with a microchannel plate intensifier. CCD detectors are described in, e.g., Bronks, et al., 1995. Anal. Chem. 65: 2750-2757. Preferably, the CCD camera uses a custom designed and fabricated CCD possessing a total of 16 million pixels (i.e., 4,000×4,000 pixel array) which can detect approximately 1% of the photons produced and can convert 40% to 80% of the photons produced into an actual measurable signal. With this system, approximately 1% of the photons produced are detected. This system can convert 40% to 80% of the photons produced into an actual measurable signal. Additionally, this CCD system possesses a minimum signal-to-noise ratio of 5:1, with a 10:1 signal-to-noise ratio being preferable. In preferred embodiments, photons are detected by a complementary metal oxide semiconductor (CMOS) sensor. Detection can occur on a CMOS array as described, for example, in Agah et al., "A High-Resolution Low-Power Oversampling ADC with Extended-Range for Bio-Sensor Arrays", *IEEE Symposium* 244-245 (2007) and Eltoukhy et al., "A 0.18 um CMOS bioluminescence detection lab-on-chip", *IEEE Journal of Solid-State Circuits* 41: 651-662 (2006), the disclosures of which are incorporated herein by reference in their entireties.

Bead-Based Pyrosequencing

In this approach, libraries may be constructed by any method that gives rise to a mixture of short, adaptor-flanked fragments. The adaptor-flanked fragments can be attached to beads such that about one fragment is attached to a bead. Clonal sequencing features can be generated by emulsion PCR, with amplicons captured to the surface of micro beads (e.g., 28 μm beads). After breaking the emulsion, the beads can be treated with denaturant to remove untethered strands, and then subjected to a hybridization-based enrichment for amplicon-bearing beads (that is, those that were present in an emulsion compartment supporting a productive PCR reaction). A sequencing primer can be hybridized to the universal adaptor at the appropriate position and orientation, that is, adjacent to or near the start of unknown sequence.

Sequencing can be performed in a flow apparatus by the pyrosequencing method. In brief, the amplicon-bearing beads can be pre-incubated with a polymerase, such as *Bacillus stearothermophilus* (Bst) polymerase, and single-stranded binding protein. The beads can then be deposited on to a microfabricated array of wells. The wells can be dimensioned such that only one nucleic-acid-containing bead typically fits in each well. Smaller beads can also be added to each well. The smaller beads either bear attached enzymes used for pyrosequencing (for example, ATP-sulfurylase and luciferase) or are blank beads used for packing. The smaller beads can also include a reversible pyrophosphate sequestering agent. It will be understood that the beads having reaction components other than the nucleic acid template need not be smaller than the nucleic acid containing beads. Beads having reaction components other than the nucleic acid template can have any of a variety of desired sizes whether smaller than, larger than or the same size as the nucleic acid containing beads. During the sequencing, one side of the array can function as a flow cell for introducing and removing sequencing reagents, whereas the other side can be aligned with a fiber-optic bundle for CCD (charge coupled device)-based or CMOS-based signal detection. At each of several hundred cycles, a single species of unlabeled nucleotide can be introduced. On templates where this results in an incorporation event, pyrophosphate is released. Via ATP-sulfurylase and luciferase, incorporation events immediately drive the generation of a burst of light, which can be detected by the CCD as corresponding to the array coordinates of specific wells. In contrast with certain other platforms, this type of sequencing is monitored in real time. Across multiple cycles (e.g., A-G-C-T-A-G-C-T . . . ), the pattern of nucleotide addition and detected incorporation events reveals the sequence of nucleic acid templates present on individual beads.

Spatial Arrangement of Sequestering and Detection Agents

Additional embodiments provided herein include spatial arrangement of sequestering agents in order to separate PPi generation and PPi detection. In some embodiments, the sequestering agent is disposed between the pyrophosphate detecting agent and the source of PPi generation. In embodiments where PPi is generated by incorporation of a nucleotide into a polynucleotide, the sequestering agent can be disposed between the polynucleotide and the detecting agent. In other words, the site of incorporation of nucleotides into the polynucleotide is separated from the detecting agent (e.g., luciferase) by the sequestering agent. Where one or more of the polynucleotide, sequestering agent and/or detecting agent are attached, or otherwise coupled, to a surface, such as a particle or bead, it will be appreciated that the particles or beads can be spatially arranged so as to locate the sequestering agent between the polynucleotide and the detecting agent.

In embodiments of the methods and systems described herein, wherein the nucleic acid to be sequenced is attached to a surface, spatial separation can be achieved by separating the nucleic acid from the detecting agent by a distance. The distance between the nucleic acid and the detecting agent can comprise sequestering agent. In some embodiments, where the nucleic acid is attached to a bead in a well, the sequestering agent can surround all or a portion of the bead so as to form a buffer between the bead surface and the detecting agent. In certain aspects, the nucleic acid to be sequenced and the synthesized polynucleotide can comprise DNA. In some embodiments, the nucleic acid to be sequenced comprises genomic DNA or cDNA. In certain aspects, the sequestering agent is disposed between the pyrophosphate detecting agent and the polynucleotide.

An example of spatial separation of the detecting agent from the site of nucleotide incorporation is set forth in FIG. 1. As shown in FIG. 1, a bead comprising polynucleotide ("DNA bead") is placed in a well in such a way that sequestering agent beads surround the DNA bead. The sequestering agent beads can be smaller than the nucleic acid bearing beads as shown in FIG. 1, or if desired, the sequestering agent beads can have a size that is similar to or even larger than the nucleic acid bearing beads. Additionally, beads having detecting agent attached thereto ("Detection beads") are disposed spatially so as to have a buffer layer of sequestering beads between the Detection beads and the DNA bead.

Non-Optical Pyrophosphate Detection

As discussed in greater detail above, pyrosequencing detects the release of inorganic pyrophosphate (PPi) as particular nucleotides are incorporated into a growing polynucleotide strand. In pyrosequencing, released PPi can be detected by being immediately converted to adenosine triphosphate (ATP) by ATP-sulfurylase, and the level of ATP generated can be detected via luciferase-produced photons.

Other methods of detecting pyrophosphate are also contemplated in the present embodiments, including the use of mass spectrometry to analyze the reaction products, the use of radiolabeled nucleotides, and detection of reaction products with "wired enzymes". Each of these non-optical detection methods is described in further detail below.

In some methods, mass spectrometry is employed to detect nucleotide incorporation in the primer extension reaction. A primer extension reaction consumes a nucleotide triphosphate, adds a single base to the primer/template duplex, and produces pyrophosphate as a by-product. Mass spectrometry can be used to detect pyrophosphate in the wash stream after a nucleotide has been incubated with the template and polymerase. The absence of pyrophosphate indicates that the nucleotide was not incorporated, whereas the presence of pyrophosphate indicates incorporation. Detection based on pyrophosphate release have been described, e.g., in WO98/13523, WO98/28440, and Ronaghi et al., Science 281:363, 1998, the content of each of which is incorporated herein by reference in its entirety.

In some methods, radiolabeled nucleotides are used. Nucleotides can be radiolabeled either in the sugar, the base, or the triphosphate group. To detect radioactivity, small radioactivity sensor can be incorporated in the substrate on which the microfluidic chip is mounted. A CCD pixel, for instance, serves as a good detector for some radioactive decay processes. Radiolabeling of the sugar or base produces an additive signal: each incorporation increases the amount of radiolabel in the primer-template duplex. If the nucleotide is labeled in the portion that is released as pyrophosphate (e.g. dNTP with $\beta$- or $\gamma$-$^{32}$P), the radioactive pyrophosphate can be detected in the wash stream. This radioactivity level is not additive, but rather binary for each attempted nucleotide addition, so subsequent addition poses no read length limit. Due to the small reagent consumption and contained nature of microfluidics, the total radioactivity used in such a system is relatively minimal, and containment is relatively simple.

In some methods, non-optical detection of pyrophosphate release makes use of "wired redox enzymes" as described, e.g., in Heller et al., Analytical Chemistry 66:2451-2457, 1994; and Ohara et al., Analytical Chemistry 65:3512-3517, 1993, each of which is incorporated herein in its entirety. Briefly, enzymes are covalently linked to a hydrogel matrix containing redox active groups capable of transporting charge. The analyte to be detected is either acted on directly by a redox enzyme (either releasing or consuming electrons) or consumed as a reagent in an enzymatic cascade that produces a substrate that is reduced or oxidized by a redox enzyme. The production or consumption of electrons is detected at a metal electrode in contact with the hydrogel. For the detection of pyrophosphate, an enzymatic cascade using pyrophosphatase, maltose phosphorylase, and glucose oxidase can be employed. Pyrophosphatase converts pyrophosphate into phosphate; maltose phosphorylase converts maltose (in the presence of phosphate) to glucose 1-phosphate and glucose. Then, glucose oxidase converts the glucose to gluconolactone and $H_2O_2$; this final reaction is the redox step which gives rise to a detectable current at the electrode. Glucose sensors based on this principle are well known in the art, and enzymatic cascades as described here have been demonstrated previously. Other enzymatic cascades besides the specific example given here are also contemplated the present embodiments. This type of detection scheme allows direct electrical readout of nucleotide incorporation at each reaction chamber, allowing easy parallelization.

Arrays

Some of the embodiments provided herein relate to arrays and methods of making arrays, useful for determining the nucleotide sequence of one or more template nucleic acids. Accordingly, provided herein is an array having a solid support having a plurality of sites distributed thereon, wherein at least a portion of the sites comprise a template nucleic acid and a pyrophosphate sequestering agent capable of reversibly sequestering pyrophosphate.

Arrays can be of various shapes and sizes but typically are flat, planar arrays having one or more flow channels. Alternatively, the arrays can have at least one surface comprising one or more depressions or wells. In some embodiments, the arrays comprise beads or particles. In certain aspects, the template nucleic acid to be sequenced is attached to a particle or bead within the well. In some embodiments, the array comprises more than one bead having a nucleic acid attached thereto. In other embodiments, the array can contain a plurality of beads. Some or all of the plurality of beads can have nucleic acids attached thereto. In such embodiments, one or more beads may have attached the same nucleic acid as another bead. In other embodiments, the attached nucleic acid can be different. In a preferred embodiment, bead arrays are constructed with bead redundancy. This means that each different nucleic acid can be present in the array on about 2 to about 200 beads. In other words, each different nucleic acid sequence can be represented about 2 to about 200 times.

In some embodiments of arrays comprising wells, the wells further comprise beads having a pyrophosphate detecting agent attached thereto. In certain aspects, the pyrophosphate sequestering agent is disposed between the template nucleic acid and the pyrophosphate detecting agent. In certain aspects, the pyrophosphate detecting agent comprises ATP-sulfurylase and luciferase, which may either be coupled to the same bead, to different beads or even to the array surface. In certain aspects, the wells further comprise packing beads.

As discussed in connection with the above-described methods, the sequestering agent can be a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or $TiO_2$. In other aspects, the pyrophosphate sequestering agent comprises hydroxyapatite. In certain aspects of the above embodiments, the pyrophosphate sequestering agent comprises particles or beads.

In embodiments where arrays comprising wells are used, the sequestering agent can be dispersed in the wells so that it surrounds or substantially covers the site of nucleotide incorporation. Sequestering agents that are powders or fine particulates can be used to coat the bottom and sides of wells or to fill in the spaces between the edges of beads and the walls of the wells. In some embodiments, the pyrophosphate sequestering agent comprises particles or beads. In such embodiments, the pyrophosphate sequestering agent can form the bead, be coated on the inner or outer surface of the bead or otherwise coupled to the bead. In embodiments where the sequestering agent comprises a bead or particle, such beads or particles are typically smaller than beads used to attach the nucleic acid to be sequenced. Typical bead size ratios range from about 1:2 to about 1:10,000. In preferred embodiments the bead ratio is about 1:2, about 1:3, about 1:4, about 1:10, about 1:20, about 1:30, about 1:40, about 1:50, about 1:100, about 1:200, about 1:500, about 1:1000, about 1:2000, about 1:5000 or about 1:10,000. However, a bead that is attached to a sequestering agent can be the same size as the nucleic acid bearing bead or even larger in size if desired.

In some embodiments of the arrays described herein, the sites of nucleotide incorporation further comprise a release reagent. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects the release reagent comprises phosphate. In other aspects the release reagent comprises a bisphosphonate. In certain aspects the release reagent is the enzyme ATP sulfurylase. In this particular aspect the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). The ATP has a lower binding affinity for the sequestering agent than does pyrophosphate.

In other embodiments, the sites further comprise a polymerase and nucleotides or nucleotide analogs.

In some embodiments, the array further comprises at least one electrode capable of producing an electric field in the presence of the sites, as set forth in greater detail hereinbelow.

Also provided are methods of making arrays. With respect to making such arrays, in a preferred embodiment, the method can include the steps of providing a solid support having a plurality of sites distributed thereon and providing a template nucleic acid and a pyrophosphate sequestering agent capable of reversibly sequestering pyrophosphate to at least a portion of the sites.

In some embodiments, the step of providing the template nucleic acid to the plurality of sites occurs prior to providing the pyrophosphate sequestering agent. In other embodiments, the step of providing the template nucleic acid to the plurality of sites occurs subsequent to providing the pyrophosphate sequestering agent. In still other embodiments, the step of providing the template nucleic acid to the plurality of sites occurs at the same time as providing the pyrophosphate sequestering agent.

As discussed in connection with the arrays described herein, the sites can comprise wells. Alternatively, the sites can be in a channel or depression. As another alternative, the sites can be positioned on a surface of a planar array.

Also as discussed in connection with the methods and systems described herein, the template nucleic acid to be sequenced can be attached to a particle or bead which can then be loaded onto the array. In a preferred embodiment, the beads are loaded into wells of the array. In a more preferred embodiment, the array is loaded such that most wells contain either one nucleic acid bead or no nucleic acid beads. In an even more preferred embodiment, most of the wells contain a single nucleic acid bead. Wells loaded with nucleic acid beads typically each contain other beads as well. However, in particular embodiments, wells need not contain any of the other types of beads described herein and can in some cases contain no other beads besides a single nucleic acid bead. In some embodiments, the beads are loaded into the wells by centrifugation. Beads can be adjusted or removed from the wells by agitation or sonication.

In some embodiments, the methods of making arrays described herein further comprise the step of providing beads having a pyrophosphate detecting agent attached thereto. In some embodiments, the pyrophosphate detecting agent can be attached directly to the wells. In some embodiments, the pyrophosphate detecting agent comprises ATP-sulfurylase and luciferase. The step of providing the beads having a pyrophosphate detecting agent to the wells can occur prior to providing the pyrophosphate sequestering agent. Alternatively, in some embodiments, the step of providing said beads having a pyrophosphate detecting agent to the wells occurs subsequent to providing the pyrophosphate sequestering agent. In still other embodiments, the step of providing said beads having a pyrophosphate detecting agent to the wells occurs at the same time as providing the pyrophosphate sequestering agent.

In addition to providing beads having a nucleic acid to be sequenced and beads having one or more components of a detecting agent, methods of making arrays described herein can include the step of providing packing beads to the wells. In some embodiments, the beads have a pyrophosphate detecting agent attached thereto and the packing beads are provided to the wells at the same time.

In certain aspects of the array manufacturing methods described herein, the sequestering agent comprises a cationic agent capable of sequestering pyrophosphate through chelation, complexation, or adsorption. In certain aspects, the cationic agent comprises an agent selected from the group consisting of a metal, metal salt, a metal oxide or other agent set forth below. In certain aspects, the metal or metal oxide comprises Ti or $TiO_2$. In other aspects, the pyrophosphate sequestering agent comprises hydroxyapatite. In certain aspects of the above embodiments, the pyrophosphate sequestering agent comprises particles or beads.

As described above, where arrays comprising wells are made, the sequestering agent can be dispersed in the wells so that it surrounds or substantially covers the site of nucleotide incorporation. Sequestering agents that are powders or fine particulates can be used to coat the bottom and sides of wells or to fill in the spaces between the edges of beads and the walls of the wells. In some embodiments, the pyrophosphate sequestering agent comprises particles or beads. In such embodiments, the pyrophosphate sequestering agent can form the bead, be coated on the inner or outer surface of the bead or otherwise coupled to the bead. In embodiments where the sequestering agent comprises a bead or particle, such beads or particles are typically smaller than beads used to attach the nucleic acid to be sequenced. Typical bead size ratios range from about 1:2 to about 1:10,000. In preferred embodiments the bead ratio is about 1:2, about 1:3, about 1:4, about 1:10, about 1:20, about 1:30, about 1:40, about 1:50, about 1:100, about 1:200, about 1:500, about 1:1000, about 1:2000, about 1:5000 or about 1:10,000. However, a bead that is attached to a sequestering agent can be the same size as the nucleic acid bearing bead or even larger in size if desired.

In some embodiments, arrays manufactured according to the methods described herein can be utilized in sequencing processes and/or pyrophosphate sequestering and release processes that include a step of providing one or more release reagents to the sites. In certain aspects, the release reagent comprises an anion capable of displacing the pyrophosphate from the sequestering agent, for example, by preferentially complexing or chelating the cation of the sequestering agent. In certain aspects, the release reagent comprises an agent selected from the group consisting of an acid or salt of an acid such as oxalic acid, an oxalate salt, sulfamic acid, a sulfamate salt, ethylene diamine tetraacetic acid (EDTA), ethylene glycol-bis-β-amino-ethyl ether N,N,N',N'-tetra-acetic acid (EGTA) citric acid, tartaric acid, acetic or other carboxylic acids or their salts. In other aspects the release reagent comprises phosphate. In other aspects the release reagent comprises a bisphosphonate. In certain aspects the release reagent is the enzyme ATP sulfurylase. In this particular aspect the ATP sulfurylase is in solution rather than being bound to a bead or other surface. The ATP sulfurylase can release the pyrophosphate from the sequestering agent by transforming the pyrophosphate into ATP in the presence of adenysine phosphosulfate (APS). The ATP has a lower binding affinity for the sequestering agent than does pyrophosphate.

In some embodiments, the method further comprises the step of providing a polymerase and nucleotides or nucleotide analogs to the sites.

Any suitable solid support can be used in the methods and systems provided herein. For example, where polynucleotides, detecting agents, enzymes, sequestering agents or release reagents are associated with a solid support, the solid support can include particles, beads, microspheres or any other suitable solid surfaces.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "Microsphere Detection Guide" from Bangs Laboratories, Fishers Ind. is a helpful guide. In preferred embodiments, beads are porous. In other preferred embodiments, the beads are controlled pore glass (CPG) beads.

Exemplary bead-based arrays that can be used in the present embodiments include, without limitation, those in which beads are associated with a solid support as described in U.S. Pat. No. 6,355,431 B1, US 2002/0102578 and PCT Publication No. WO 00/63437, each of which is incorporated herein by reference in its entirety.

The beads need not be spherical; irregular particles may be used. In addition, the beads may be porous, thus increasing the surface area of the bead available for assay. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used. An array of beads useful in the present embodiments can also be in a fluid format such as a fluid stream of a flow cytometer or similar device. Exemplary formats that can be used in the present embodiments to distinguish beads in a fluid sample using microfluidic devices are described, for example, in U.S. Pat. No. 6,524,793, incorporated herein by reference in its entirety. Commercially available fluid formats for distinguishing beads include, for example, those used in XMAP™ technologies from Luminex or MPSS™ methods from Lynx Therapeutics.

Electric Field Assisted Delivery

In certain aspects of the above embodiments, the step of providing a reagent bead or other substance to an array can include applying a voltage to the plurality of sites of the array. For example, where beads and reagents are provided to an array comprising wells, an advantage can be achieved by applying an electric field (e-field) to facilitate bead loading, reagent delivery and washing of the byproducts. To implement e-field assisted (EFA) bead and reagent delivery and washing on the surface of an array, electrodes can be fabricated at the bottom of the wells. The electrodes can be of any suitable material or thickness. For example, in one embodiment, a bottom electrode can be deposited and etched from a conducting layer (a few hundred nm of platinum) on the bottom side of a well. A second electrode can be disposed above the well. In embodiments where wells are part of a fluidic chamber, the second electrode can be deposited as a blanket layer on the top cover of the fluidic chamber. Voltage can be applied between these electrodes (formed as such at the top and bottom of the fluidic chamber) in order to form the e-field.

The e-field can be used to draw beads and reagents for faster and more efficient bead loading or delivery. As an example, selective trapping of 28 μm Sepharose beads inside wells with microfabricated electrodes can be performed. A potential difference of ~1 V can then applied across these electrodes. This voltage is small enough to avoid any electrolytic reaction and high enough to achieve an electric field of around 100 V/cm.

Furthermore, e-field assistance can also be employed to achieve active pre-concentration of the nucleotides near the reaction wells. Such localized concentration technique allows the use of less concentrated nucleotides with faster and enhanced nucleotide delivery into the reaction chambers. Using this concept, reagent amount can be reduced.

The use of an applied e-field has several other advantages, for example, PPi released during each pyrosequencing run can be confined to the reaction well by the electric field and chemical crosstalk between two adjacent wells can be minimized.

Electric Field Assisted Washing

A factor that promotes out-of-phase or non-specific incorporation is incomplete removal of excess nucleotides. This can be detrimental to long reads and thus washing cycles are typically utilized. Accordingly, the methods provided herein can further comprise washing steps. Addition of pyrophosphatase increases the washing efficiency of the reaction by shutting down the luminescent regenerative cycle more quickly than apyrase alone. Furthermore, to generate longer read lengths, accumulation of washing enzymes, such as apyrase and pyrophosphatase, can pose problems by affecting nucleotide incorporation efficiency. Therefore, inhibitors such as sodium azide can be added to quench any remaining washing enzymes in the system.

In some embodiments of the methods and systems described herein, the washing step comprises electric-field assisted (EFA) removal of pyrophosphate from the sequestering agent. To implement EFA bead and reagent delivery and washing on the surface of an array, electrodes can be fabricated at the bottom of the wells. The electrodes can be of any suitable material or thickness. For example, in one embodiment, a bottom electrode can be deposited and etched from a conducting layer (a few hundred nm of platinum) on the bottom side of a well. A second electrode can be disposed above the well. In embodiments where wells are part of a fluidic chamber, the second electrode can be deposited as a blanket layer on the top cover of the fluidic chamber. Voltage can be applied between these electrodes (formed as such at the top and bottom of the fluidic chamber) in order to form the e-field.

EXAMPLES

Example 1

Reversible Sequestration of PPi

Reversible PPi sequestering was demonstrated in the following experiment. A luminometer was used to detect luminescence in wells of a multi-well plate. A first well was prepared containing assay buffer and 0.5 micromolar pyrophosphate. Then 1 microliter of enzyme beads was added. Via a flow system, 200 microliter of substrate buffer was added to initiate the luminescence. The well generated a luminescence reading of ca. 480,000 units.

In a second well the same experiment was performed but without any added pyrophosphate. The well generated a luminescence reading of 800 units, indicating the background level of luminescence.

In a third well the same experiment was performed as in the first well, but before adding the enzyme beads, $TiO_2$ particles were added. The well generated a luminescence reading of 28,000 units.

In a fourth well the same experiment was performed as in the third well, but after the $TiO_2$ was added and stirred, sodium oxalate was added to release the pyrophosphate. The flow systems added the substrate buffer and the well generated a luminescence reading of 240,000 units. The results are summarized in the table below.

| Well | Components | Luminometer Reading |
|---|---|---|
| 1 | Assay buffer<br>PPi | 480,000 |
| 2 | Assay buffer | 800 |
| 3 | Assay buffer<br>PPi<br>TiO2 | 28,000 |
| 4 | Assay buffer<br>PPi<br>TIO2<br>Sodium oxalate | 240,000 |

Among other things, this experiment demonstrates that PPi can be sequestered with titanium dioxide and released with sodium oxalate. This experiment also shows that the sodium oxalate does not chelate all of the magnesium present in the reaction mixtures and that the sulfurylase and luciferase survived the treatment with $TiO_2$ and still functioned.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method of delaying pyrophosphate detection comprising:
   providing a pyrophosphate sequestering agent;
   generating pyrophosphate in the presence of said sequestering agent, wherein generating pyrophosphate in the presence of said sequestering agent comprises incorporating a nucleotide or nucleotide analog into a polynucleotide, whereby said pyrophosphate is reversibly sequestered;
   releasing said pyrophosphate from said sequestering agent; and
   detecting said pyrophosphate.

2. The method of claim 1, wherein said pyrophosphate is reversibly sequestered by adsorption onto said sequestering agent.

3. The method of claim 2, wherein said pyrophosphate sequestering agent comprises a cationic agent.

4. The method of claim 3, wherein said cationic agent comprises an agent selected from the group consisting of a metal ion, a metal salt, a metal oxide, hydroxyapatite, ammonium, a substituted ammonium salt, or a resin or bead comprising ammonium or a substituted ammonium salt.

5. The method of claim 4, wherein said metal ion, metal salt or metal oxide comprises Ti ion or TiO2.

6. The method of claim 2, wherein said pyrophosphate sequestering agent comprises particles or beads.

7. The method of claim 1, wherein releasing the pyrophosphate from said sequestering agent comprises providing a release reagent to said sequestering agent.

8. The method of claim 7, wherein said release reagent comprises an anionic agent.

9. The method of claim 8, wherein said anionic agent comprises an agent selected from the group consisting of oxalic acid, an oxalate salt, sulfamic acid, a sulfamate salt, ethylene diamine tetraacetic acid (EDTA), and ethylene glycol-bis-β-amino-ethyl ether N, N, N', N'-tetra-acetic acid (EGTA).

10. The method of claim 7, wherein said release reagent comprises phosphate, bisphosphonate, or ATP sulfurylase.

11. The method of claim 10, wherein said ATP sulfurylase is in solution.

12. The method of claim 1, wherein detecting said pyrophosphate comprises providing a pyrophosphate detecting agent.

13. The method of claim 12, wherein said pyrophosphate detecting agent comprises luciferase.

14. The method of claim 13, wherein said pyrophosphate detecting agent further comprises ATP sulfurylase.

15. The method of claim 13, wherein said luciferase is attached to a bead.

16. The method of claim 14, wherein said ATP sulfurylase is attached to a bead.

17. The method of claim 16, wherein said ATP sulfurylase and said luciferase are both attached to the same bead.

18. The method of claim 1, wherein said polynucleotide is attached to a surface.

19. The method of claim 18, wherein said surface comprises a bead or a well.

20. The method of claim 1, further comprising the step of washing said sequestering agent.

21. The method of claim 20, wherein washing comprises adding a washing enzyme to said sequestering agent.

22. The method of claim 21, wherein said washing enzyme is selected from the group consisting of pyrophosphatase, apyrase, alkaline phosphatase and ATP sulfurylase.

23. The method of claim 21, further comprising adding a washing enzyme inhibitor to said sequestering agent.

24. The method of claim 23, wherein said washing enzyme inhibitor is sodium azide.

25. The method of claim 20, wherein said washing step comprises electric-field assisted removal of pyrophosphate from said sequestering agent.

26. A method for sequencing a nucleic acid, said method comprising:
   providing nucleotides or nucleotide analogs in the presence of a pyrophosphate sequestering agent and a pyrophosphate detecting agent;
   incorporating one or more of said nucleotides or nucleotide analogs into a polynucleotide so as to extend said polynucleotide in the presence of said pyrophosphate sequestering agent, thereby generating sequestered pyrophosphate;
   removing said unincorporated nucleotides or nucleotide analogs from the presence of said pyrophosphate detecting agent;
   releasing said pyrophosphate from said sequestering agent in the presence of said pyrophosphate detecting agent; and
   detecting released pyrophosphate, wherein released pyrophosphate indicates that one or more nucleotides or nucleotide analogs have been incorporated into said polynucleotide.

27. A method of modulating the availability of free pyrophosphate during sequencing of a nucleic acid molecule, said method comprising:
   combining nucleotides or nucleotide analogs with a nucleic acid template;
   incubating the nucleic acid template and said nucleotides or nucleotide analogs together with a polymerase and a pyrophosphate sequestering agent under conditions sufficient to form a polynucleotide complementary to all or a portion of the nucleic acid template, wherein pyrophosphate generated during said incubating is reversibly sequestered by the sequestering agent;
   removing from said nucleic acid template the nucleotides or nucleotide analogs that have not been incorporated into the polynucleotide; and
   releasing said pyrophosphate from said pyrophosphate sequestering agent by providing a release reagent.

28. The method of claim 26, wherein said pyrophosphate is reversibly sequestered by adsorption onto said sequestering agent.

29. The method of claim 28, wherein said pyrophosphate sequestering agent comprises a cationic agent.

30. The method of claim 29, wherein said cationic agent comprises an agent selected from the group consisting of a metal ion, a metal salt and a metal oxide.

31. The method of claim 30, wherein said metal ion, metal salt or metal oxide comprises Ti ion or TiO2.

32. The method of claim 28, wherein said sequestering agent comprises particles or beads.

33. The method of claim 26, wherein releasing the pyrophosphate from said sequestering agent comprises providing a release reagent to said sequestering agent.

34. The method of claim 33, wherein said release reagent comprises an anionic agent.

35. The method of claim 33, wherein said release reagent comprises phosphate.

36. The method of claim 26, wherein said pyrophosphate detecting agent comprises luciferase.

37. The method of claim 36, wherein said pyrophosphate detecting agent further comprises ATP sulfurylase.

38. The method of claim 26, wherein said polynucleotide is attached to a surface.

39. The method of claim 27, further comprising providing a pyrophosphate detecting agent, thereby detecting pyrophosphate that is released from said pyrophosphate sequestering agent.

40. The method of claim 27, wherein said pyrophosphate sequestering agent comprises a cationic agent.

41. The method of claim 40, wherein said cationic agent comprises an agent selected from the group consisting of a metal ion, a metal salt and a metal oxide.

42. The method of claim 41 wherein said metal ion, metal salt or metal oxide comprises Ti ion or $TiO_2$.

43. The method of claim 27, wherein said sequestering agent comprises particles or beads.

44. The method of claim 27, wherein said release reagent comprises an anionic agent.

45. The method of claim 27, wherein said release reagent comprises phosphate.

46. The method of claim 27, wherein said pyrophosphate detecting agent comprises luciferase.

47. The method of claim 46, wherein said pyrophosphate detecting agent further comprises ATP sulfurylase.

48. The method of claim 27, wherein said polynucleotide is attached to a surface.

* * * * *